United States Patent
Kim et al.

(10) Patent No.: US 8,227,418 B2
(45) Date of Patent: Jul. 24, 2012

(54) ALPHA-DEFENSINS AS ANTHRAX IMMUNOTHERAPEUTICS

(75) Inventors: Chun Kim, Berlin (DE); Stefan Kaufmann, Berlin (DE); Nadesan Gajendran, Potsdam (DE)

(73) Assignee: Max-Planck-Gesellschaft zur Foderung der Wissenschaften E.V., Berlin (DE)

( * ) Notice: Subject to any disclaimer, the term of this patent is extended or adjusted under 35 U.S.C. 154(b) by 1558 days.

(21) Appl. No.: 11/632,956

(22) PCT Filed: Jul. 21, 2005

(86) PCT No.: PCT/EP2005/007967
§ 371 (c)(1),
(2), (4) Date: Jan. 19, 2007

(87) PCT Pub. No.: WO2006/008162
PCT Pub. Date: Jan. 26, 2006

(65) Prior Publication Data
US 2010/0143416 A1 Jun. 10, 2010

(30) Foreign Application Priority Data
Jul. 22, 2004 (EP) .................................. 04017392

(51) Int. Cl.
*A61K 38/16* (2006.01)
*A61K 38/00* (2006.01)
*A01N 63/00* (2006.01)
*A01N 37/18* (2006.01)

(52) U.S. Cl. ........ 514/21.2; 514/2.3; 514/152; 424/93.4; 424/93.46; 424/246.1

(58) Field of Classification Search ........................ None
See application file for complete search history.

(56) References Cited

U.S. PATENT DOCUMENTS

| | | |
|---|---|---|
| 5,242,902 A | 9/1993 | Murphy et al. |
| 2004/0018193 A1 | 1/2004 | Alibek et al. |

OTHER PUBLICATIONS

Varma, 1997, Nature, vol. 389, pp. 239-242.*
Lowenberger et al., "Insect Immunity: Isolation of Three Novel Inducible Antibacterial Defensins from the Vector Mosquito, Aedes Aegypti," *Insect Biochem. Molec. Biol.*, vol. 25, No. 7, pp. 867-873, 1995.
Wilde et al., "Purification and Characterization of Human Neutrophil Peptide 4, A Novel Member of the Defensin Family," *Journal of Biological Chemistry*, vol. 264, No. 19, pp. 11200-11203, 1989.

* cited by examiner

*Primary Examiner* — Robert Landsman
*Assistant Examiner* — Ian Dang
(74) *Attorney, Agent, or Firm* — Foley & Lardner LLP

(57) ABSTRACT

The present invention relates to the use of an alpha-defensin in the manufacture of a medicament for the treatment, amelioration or prevention of a disease caused by *Bacillus anthracis* (*B anthracis*) infection. Furthermore, methods for the treatment of an *B. anthracis* infection as well as methods of protection against a *B. anthracis* infection, e.g. a vaccination are described.

9 Claims, 6 Drawing Sheets

Figure 3:
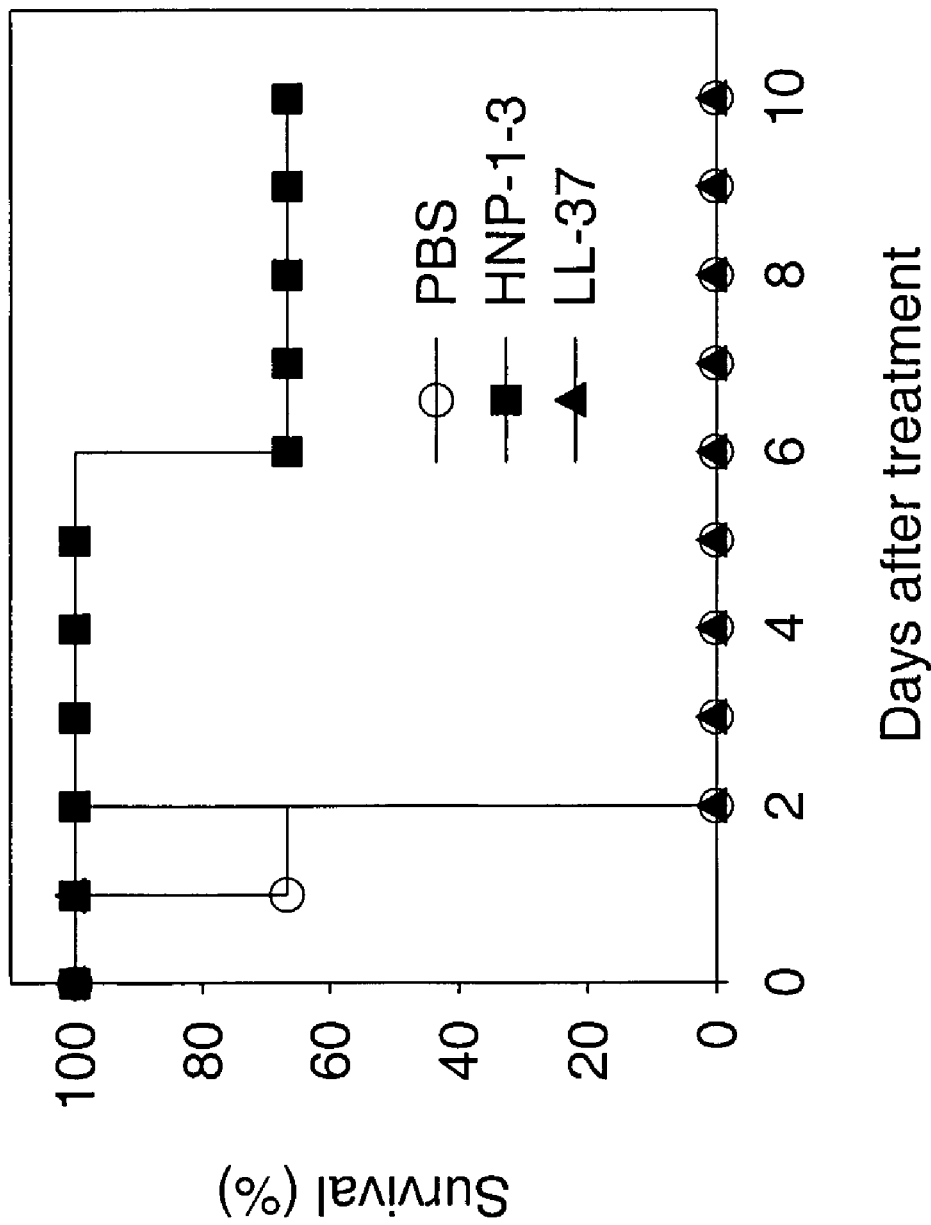

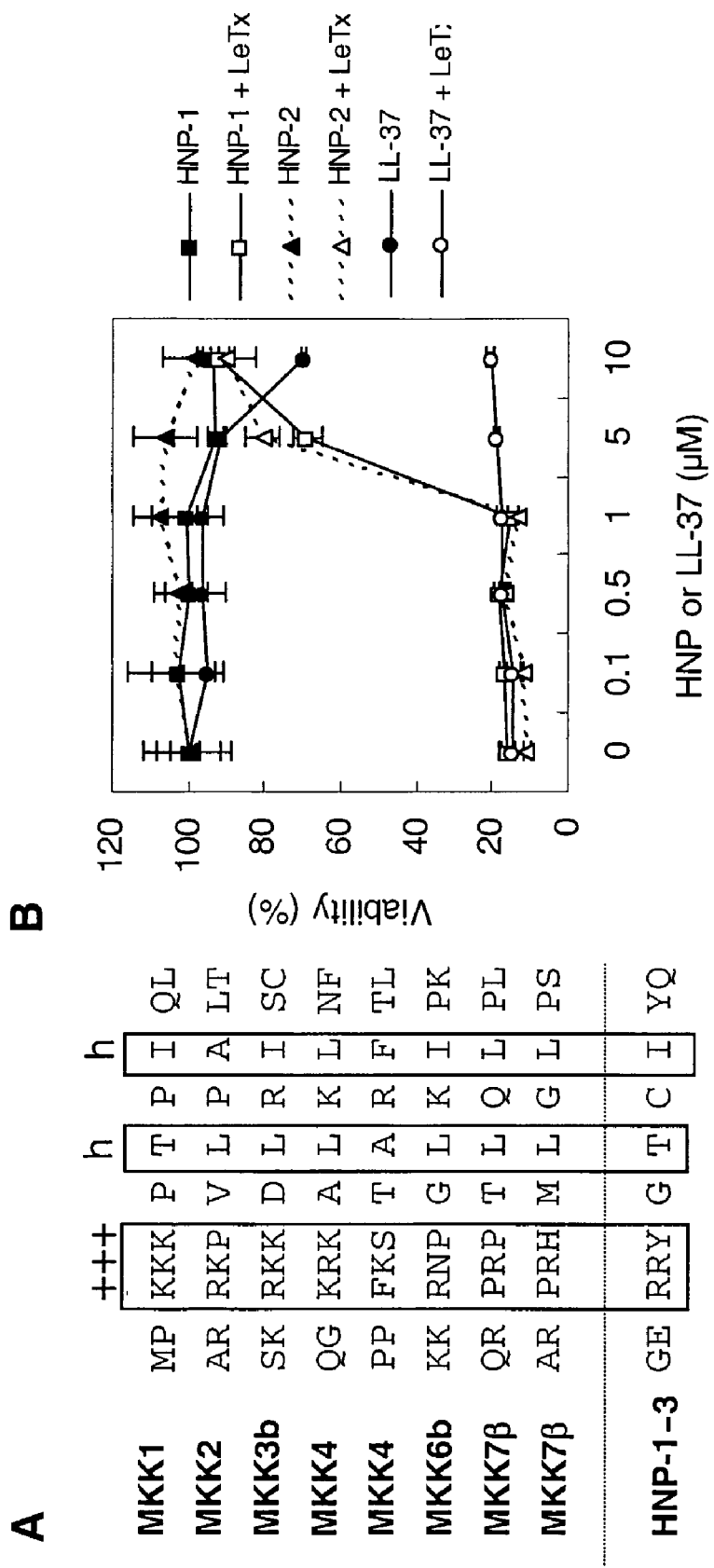
Fig. 1 (A-B)

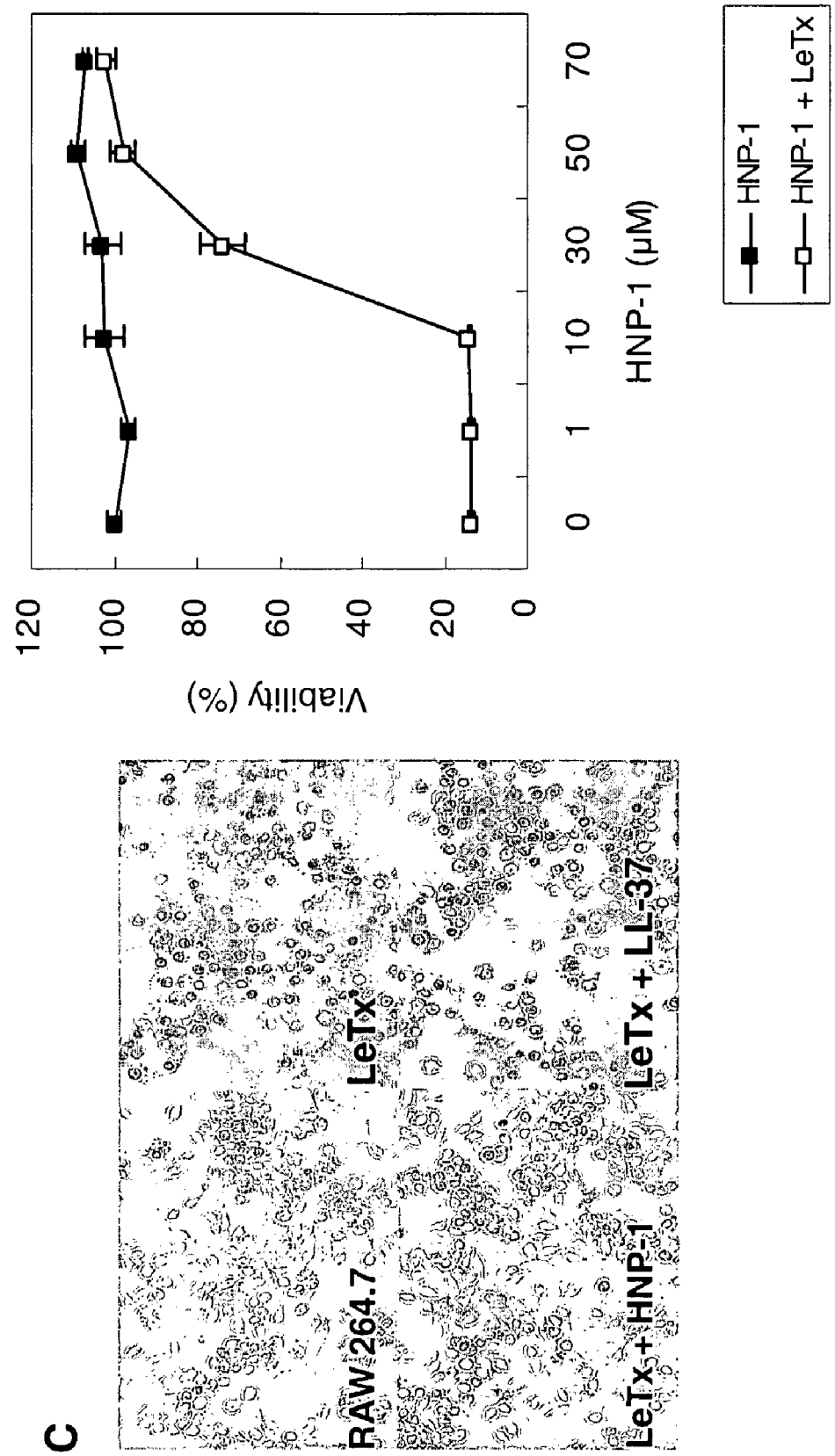
Fig. 1 (C-D)

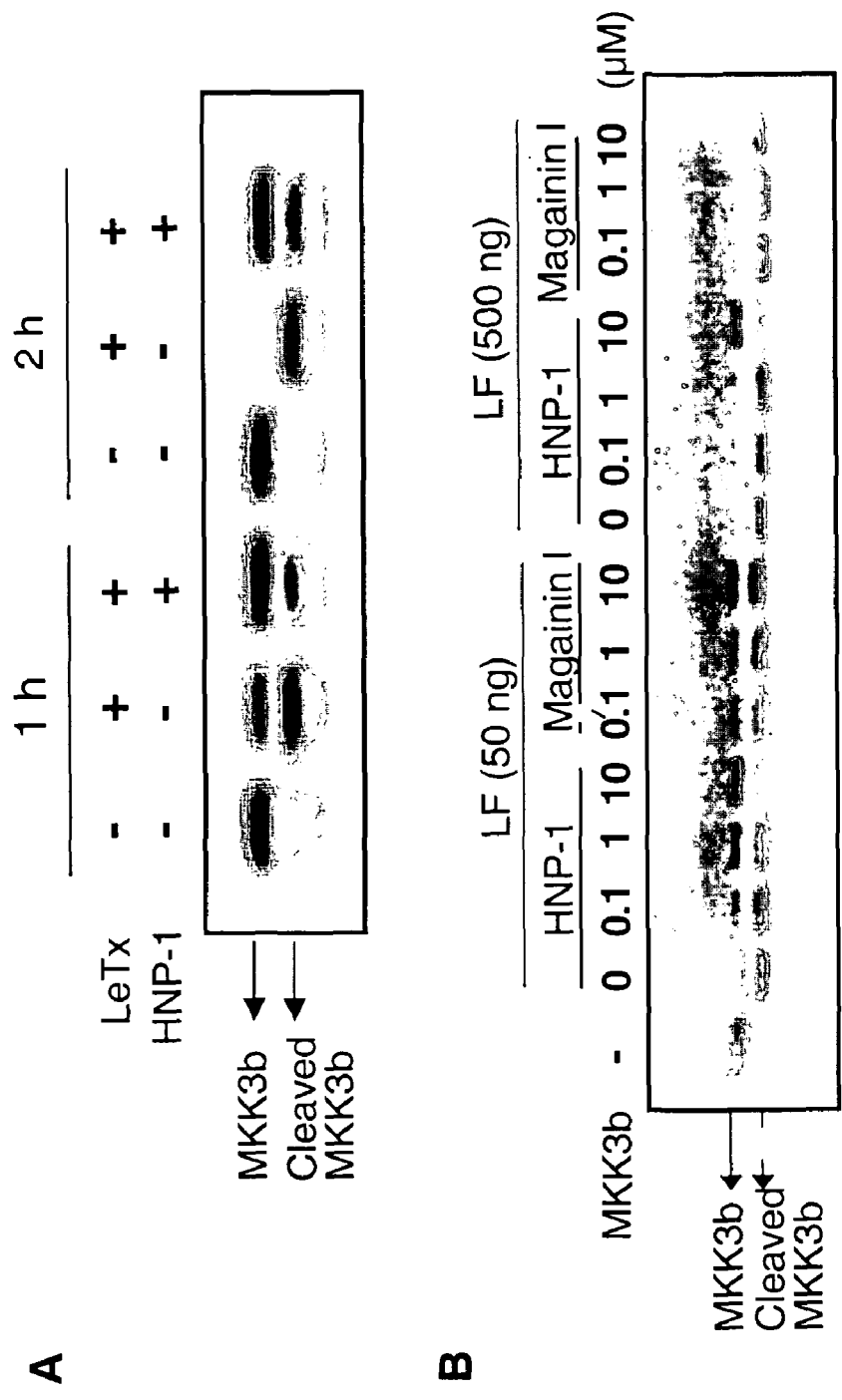
Fig. 2 (A-B)

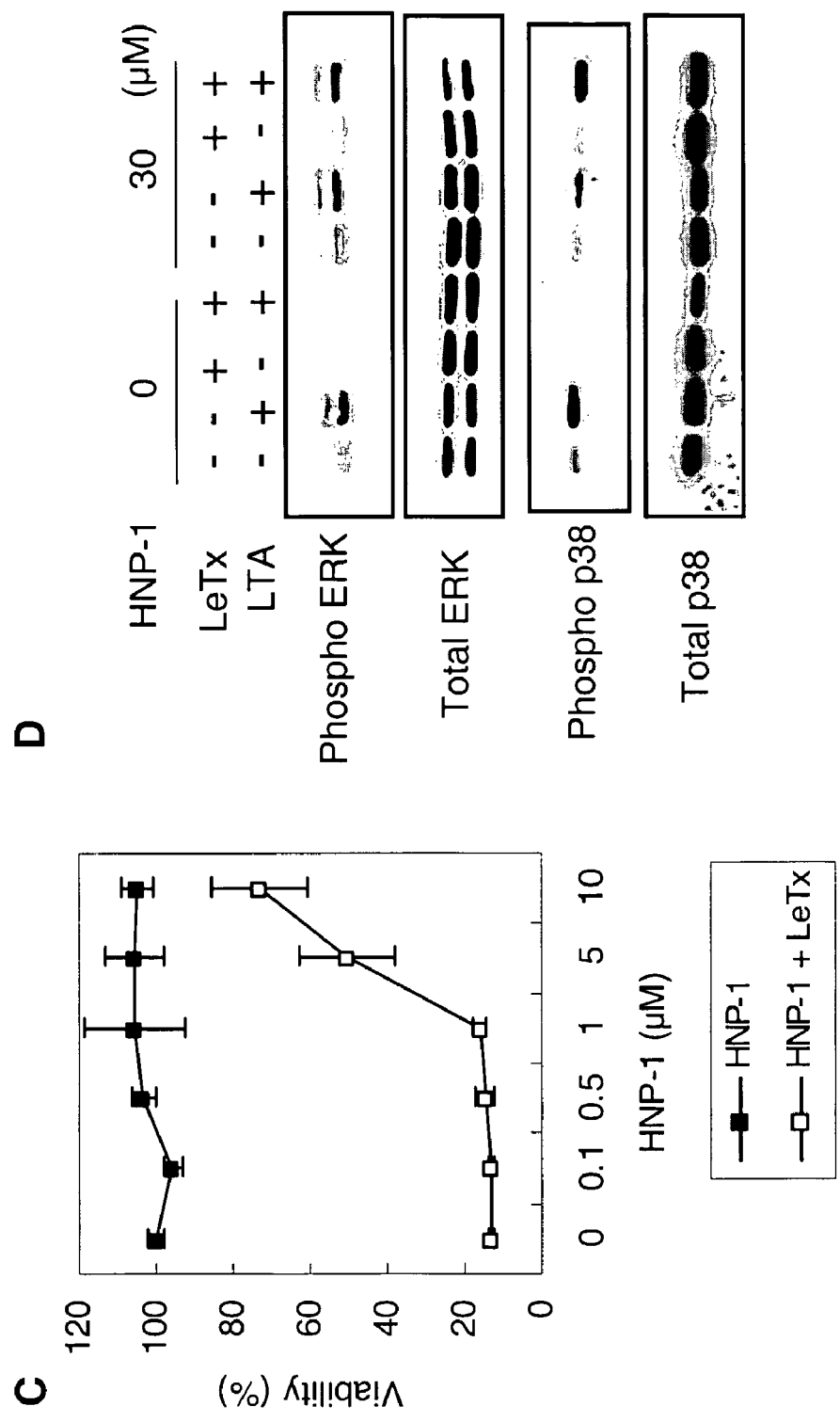
Fig. 2 (C-D)

Fig. 4

```
                                              1         2         3         4         5    6
Human:
HNP1       A C Y C R I P A C I A G E R R Y G T C I Y Q G R L W A F C C
HNP2         C Y C R I P A C I A G E R R Y G T C I Y Q G R L W A F C C
HNP3       D C Y C R I P A C I A G E R R Y G T C I Y Q G R L W A F C C
HNP4       V C Y C R   P A C   A G E R R Y G T C   Y Q G R L W A F C C   V
Rabbit:
NP1        V   C   C R   L V F C   L L F   R R T   G V C   L I G   V L W   S F T Y   T   C C T R
NP2        V V S A C R R A L L   F L L   E L L S R T R L R N C   H I R R   V R R   H P L L   C C C R R
NP3a       G G A A C R R A   R F L L R G E R R F G G C G Y R R R A R R V V R R G   R H Y F P V L L C C C R S
NP3b       V V A A C R R R Q L L   S L R L E R R F G G C G Y R R R K T R R A G G R R H Y P L L L C C C P R R
NP4        V V T A C R R R F G F L L R R R A A S G G C G Y N R H V T A G G N R R H T L L L C C C R R
NP5        V V T T C R R G F F L L   R R R A A S G G C G Y N R R V T A R R F R H T L L L C C C R R
Rat:
RtNP1      T T C Y C R R T R G F R R E E R R L L S G G C G R L N V A R R A I Y R L R L C C C R R
RtNP2      V V C Y S T S R G S   F G R E E R R L L S G G C G R L N G A R R R I Y R L R L C C C R R
RtNP3        V S Y C T   G A C R F L F R G E R R L L S G G C G V S R T A G G R V   Y R L L L C C C R R
RtNP4      T T C Y C R R S A F L S G F R R E E R R L L T G G C G T V T A G R L   Y R L L L C C C R R
Mouse:
CRYPT      A C   C R G R C   Y G C   N R G M N G T   K G R M N G T   G G R L   Y T L   L C C C R
Guinea pig:
GNP        L R D L R R C I T T R T C R F P Y R R L G T C I F Q N R V Y T F C C
```

ALPHA-DEFENSINS AS ANTHRAX IMMUNOTHERAPEUTICS

The present invention relates to the use of an alpha-defensin in the manufacture of a medicament for the treatment, amelioration or prevention of a disease caused by *Bacillus anthracis* (*B. anthracis*) infection. Furthermore, methods for the treatment of an *B. anthracis* infection as well as methods of protection against a *B. anthracis* infection, e.g. a vaccination are described.

As laid down by Cieslak in "Emerging Infectious Diseases" in 1999, anthrax is one of the great infectious diseases of antiquity; National Symposium on Medical and Public Health Response in Bioterrorism; 1999, Arlington, Va., USA. The "Black Bane," a disease that swept through Europe in the 1600s causing large numbers of human and animal deaths, was likely anthrax. In 1876, anthrax became the first disease to fulfill Koch's postulates (i.e., the first disease for which a microbial etiology was firmly established), and 5 years later, in 1881, the first bacterial disease for which immunization was available. Large anthrax outbreaks in humans have occurred throughout the modern era—more than 6,000 (mostly cutaneous) cases occurred in Zimbabwe between October 1979 and March 1980, and 25 cutaneous cases occurred in Paraguay in 1987 after the slaughter of a single infected cow. Anthrax, in the minds of most military and counterterrorism planners, represents the single greatest biological warfare threat.

Anthrax spores lend themselves well to aerosolization and resist environmental degradation. Moreover, these spores, at 2-6 microns in diameter, are the ideal size for impinging on human lower respiratory mucosa, optimizing the chance for infection. It is the manufacture and delivery of anthrax spores in this particular size range (avoiding clumping in larger particles) that presents a substantial challenge to the terrorist attempting to use the agent as a weapon. The milling process imparts a static charge to small anthrax particles, making them more difficult to work with and, perhaps, enabling them to bind to soil particles. This, in part, may account for the relatively low secondary aerosolization potential of anthrax, as released spores bind to soil, now clumping in particles substantially in excess of 6 microns. This clumping tendency, together with a high estimated $ID_{50}$ of 8,000-10,000 spores may help explain the rarity of human anthrax in most of the Western world, even in areas of high soil contamination. Other potential bioweapons, such as Q fever and tularemia, have $ID_{50}$ values as low as 1 and 10 organisms, respectively.

Most endemic anthrax cases are cutaneous and are contracted by close contact of abraded skin with products derived from infected herbivores, principally cattle, sheep, and goats. Such products might include hides, hair, wool, bone, and meat.

Inhalational anthrax, also known as woolsorters' disease, has been an occupational hazard of slaughterhouse and textile workers; immunization of such workers has all but eliminated this hazard in Western nations. As a weapon, however, anthrax would likely be delivered by aerosol and, consequently, be acquired by inhalation. A third type of anthrax, acquired through the gastrointestinal route (e.g., consuming contaminated meat) is exceedingly rare but was initially offered by Soviet scientists as an explanation for the Sverdlovsk outbreak. Inhalational anthrax begins after exposure to the necessary inoculum, with the uptake of spores by pulmonary macrophages. These macrophages carry the spores to tracheobronchial or mediastinal lymph nodes. Here, *B. anthracis* finds a favorable milieu for growth and is induced to vegetate. The organism begins to produce an antiphagocytic capsule and at least three proteins, which appear to play a major role in virulence. These proteins are known as edema factor (EF), lethal factor (LF), and protective antigen (PA). Lethal toxin (LeTx), the combination of lethal factor (LF) and protective antigen (PA), plays a major role in anthrax pathogenesis and is critical for its high lethality.

*B. anthracis* produces a toxin consisting of three proteins: LF, PA and edema factor (EF). Individually, none of these proteins is toxic. However, the combination of LF and PA, called LeTx, and that of EF and PA, called edema toxin (EdTx) are highly toxic to mammalian hosts; Collier (2003) *Annu Rev Cell Dev Biol* 19, 45. LF is a metalloprotease, which cleaves certain MKKs, causing death of experimental animals; Duesbery (1998). *Science* 280, 734.) EF, a calmodulin- and $Ca^{2+}$-dependent adenylate cyclase (Leppla, (1982) *Proc Natl Acad Sci USA* 79, 3162), is responsible for edema. PA promotes transport of the other two proteins into host cells by receptor mediated endocytosis; Bradley, (2001), *Nature* 414, 225.

Inactivation of the LF gene in *B. anthracis* reduces virulence more than 1000-fold suggesting that anthrax pathology is largely determined by LF; Pezard (1991), *Infect Immun* 59, 3472. The identified substrates of LF have the consensus sequence, ++++xhx↓h, where '+' represents a basic residue, 'h' stands for a hydrophobic amino acid, and '↓' indicates the cleavage site; Vitale (2000), *Biochem J* 352 Pt 3, 739.

According to a LF structure study, the cluster of acidic residues in active center show the preference for basic residues in the substrates and the substrates should bind with antiparallel β-sheet formation to LF; Pannifer (2001) *Nature* 414, 229.

Accordingly, *B. anthracis*, like certain other Bacteria, produces toxins. Even elimination of bacteria after an infection results in disease caused by said toxins. Therefore, a problem underlying the present invention is to provide for means and methods which improve the medical situation of patients infected with *B. anthracis*.

The technical problem is solved by the embodiments as characterized herein below and in the claims.

Accordingly, the present invention relates to the use of an alpha-defensin in the manufacture of a medicament for the treatment, amelioration or prevention of a disease caused by *Bacillus anthracis* (*B. anthracis*) infection.

In accordance with this invention, it was surprisingly found that intoxication by bacterial pathogens can be prevented by neutralization or inactivating toxin activity, in particular in conjunction with chemotherapy comprising, inter alia, the use of antibiotics. In contrast to other infections, like infections with, e.g., *S. aureus*, an infection with *B. anthracis* can not simply be eradicated by killing the bacteria, for example by single use of antibiotics. In *B. anthracis* infections, eradication of the bacteria by, e.g. antibiotics after the above described toxins have been produces has no protective consequences, since the toxin circulates in the body and exerts its toxic effects.

The present invention provides for the use of an alpha-defensin in the medical intervention of an *B. anthracis* infection and in particular in the medical intervention of anthrax. Said alpha-defensin, in a particular said HNP (as will be detailed below) may be used in the medicament in form of its amino acid sequence (i.e. as peptide) as well as in form of a nucleic acid sequence (i.e. in form of a nucleic acid molecules which encodes an alpha-defensins/HNPs as defined herein.). Nucleic acid molecules are particularly useful in gene therapy approaches.

Alpha-defensins are well known in the art and, inter alia, described in Ganz, Nat. Rev. Immunol 3 (2003), 710 and Lehrer, Ann. Rev. Immunol. 11 (1993), 105-128. Defensins are a family of peptides with a characteristic beta-sheet rich fold and three dsislufide bridges, linked by six cysteins. In the defensin family, three subfamilies are known: alpha-, beta-, and theta-defensins. As far as the alpha defensins are concerned, in humans six have been identified (Lehrer, (1993) loc. cit.), whereby four of these six are produced by granulocytes and lymphocytes. These four are known in the art as human neutrophil protein, HNP1, 2, 3 and 4.

Accordingly, in a preferred embodiment of this invention, the alpha-defensin to be employed in the use for the preparation of a medicament/pharmaceutical composition is a human neutrophil protein (HNP), wherein, even more preferably said HNP is selected from an alpha-defensin naturally produced by granulocyte and lymphocyte and is preferably selected from the group consisting of HNP-1, HNP-2, HNP-3 and HNP-4. Yet, in accordance with the technical results presented herein, most preferred are in context of this invention the HNPs 1, 2 and 3.

Most preferably, the alpha-defensin or the HNP to be used in the preparation of a pharmaceutical composition/medicament is selected from the group consisting of (a) a polypeptide/peptide encoded by a nucleic acid molecule comprising a nucleic acid molecule encoding the peptide having an amino acid sequence as shown in SEQ ID NO: 2, SEQ ID NO: 4, SEQ ID NO: 6 or SEQ ID NO: 8;

(b) a polypeptide/peptide encoded by a nucleic acid molecule having the DNA sequence as shown in SEQ ID NOS: 1, 3, 5 or SEQ ID NO: 7;

(c) a polypeptide/peptide encoded by a nucleic acid molecule hybridizing to the complementary strand of nucleic acid molecules as defined in (a) or (b) and encoding a functional alpha-defensis or a functional fragment thereof; and (d) a polypeptide/peptide encoded by a nucleic acid molecule being degenerate as a result of the genetic code to the nucleotide sequence of a nucleic acid molecule as defined in (c).

SEQ ID NOs. 1 and 2 relate to HNP1 and are as follows:

```
SEQ ID NO: 1 "HNP-1 nucleotide sequence"
Coding Sequence  position 81 to 365
Signal peptide   position 81 to 137
Proprotein       position 138 to 362
Mature peptide   position 273 to 362
Poly A signal    position 466 to 471

1 ctatagaaga cctgggacag aggactgctg tctgccctct ctggtcaccc tgcctagcta
 61 gaggatctgt gacccccagcc atgaggaccc tcgccatcct tgctgccatt ctcctggtgg
121 ccctgcaggc ccaggctgag ccactccagg caagagctga tgaggttgct gcagccccgg
181 agcagattgc agcggacatc ccagaagtgg ttgtttccct tgcatgggac gaaagcttgg
241 ctccaaagca tccaggctca aggaaaaaca tggcctgcta ttgcagaata ccagcgtgca
301 ttgcaggaga acgtcgctat ggaacctgca tctaccaggg aagactctgg gcattctgct
361 gctgagcttg cagaaaaaga aaaatgagct caaaatttgc tttgagagct acagggaatt
421 gctattactc ctgtaccttc tgctcaattt cctttcctca tcccaaataa atgccttggt
481 acaagaaaag The codon "tga" on position 363 to 365 is the stop codon.

SEQ ID NO: 2 "Amino Acid sequence of HNP1"
Signal peptide  position 1 to 19
Propeptide      position 20 to 94
Mature peptide  position 65 to 94

1 mrtlailaai llvalqaqae plqaradeva aapeqiaadi pevvvslawd eslapkhpgs
 61 rknmacycri paciagerry gtciyqgrlw afcc
```

SEQ ID NOs. 3 and 4 relate to HNP2 and are as follows:

```
SEQ ID NO: 3 "HNP-2 nucleic acid sequence coding
for HNP-2"

HNP-2 is a proteolytic product of HNP-1, HNP-3 or
both. A corresponding nucleic acid sequence coding
for HNP-2 is tgctattgca gaataccagc gtgcattgca ggagaacgtc
gctatggaac ctgcatctac cagggaagac tctgggcatt
ctgctgc  (Artificial sequence)

SEQ ID NO: 4: "Amino Acid sequence of mature
HNP-2"

cycri paciagerry gtciyqgrlw afcc
```

SEQ ID NOs. 5 and 6 relate to HNP3 and are as follows:

SEQ ID NO: 5: "nucleotide sequence coding for HNP-3"

```
Codig sequence position 86 to 370
Signal peptide position 86 to 142
Proprotein      position 143 to 367
Mature peptide  position 278 to 367
Poly A signal   position 471 to 476

1 ccttgctata gaagacctgg gacagaggac tgctgtctgc cctctctggt caccctgcct
 61 agctagagga tctgtgaccc cagccatgag gaccctcgcc atccttgctg ccattctcct
121 ggtggccctg caggcccagg ctgagccact ccaggcaaga gctgatgagg ttgctgcagc
181 cccggagcag attgcagcgg acatcccaga agtggttgtt tcccttgcat gggacgaaag
241 cttggctcca aagcatccag gctcaaggaa aaacatggac tgctattgca gaataccagc
301 gtgcattgca ggagaacgtc gctatggaac ctgcatctac cagggaagac tctgggcatt
361 ctgctgctga gcttgcagaa aagaaaaat gagctcaaaa tttgctttga gagctacagg
421 gaattgctat tactcctgta ccttctgctc aatttccttt cctcatctca aataaatgcc
481 ttgttac
```

The codon "tga" on position 368 to 370 is the stop codon.

SEQ ID NO: 6: "Amino Acid sequence of HNP-3"

```
Signal peptide position 1 to 19
Proprotein     position 20 to 94
Mature peptide position 65 to 94

1 mrtlailaai llvalqaqae plqaradeva aapeqiaadi pevvvslawd eslapkhpgs
61 rknmdcycri paciagerry gtciyqgrlw afcc
```

SEQ ID NOs: 7 and 8 relate to HNP4 and are as follows:

SEQ ID NO: 7: "HNP-4 nucleotide sequence"

```
Coding sequence position 52 to 345
Signal peptide  position 52 to 108
Proprotein      position 109 to 342
Mature peptide  position 241 to 342

1 gtctgccctc tctgctcgcc ctgcctagct tgaggatctg tcacccagc catgaggatt
 61 atcgccctcc tcgctgctat tctcttggta gccctccagg tccgggcagg cccactccag
121 gcaagaggtg atgaggctcc aggccaggag cagcgtgggc cagaagacca ggacatatct
181 atttcctttg catgggataa aagctctgct cttcaggttt caggctcaac aaggggcatg
241 gtctgctctt gcagattagt attctgccgg cgaacagaac ttcgtgttgg gaactgcctc
301 attggtggtg tgagtttcac atactgctgc acgcgtgtcg attaacgttc tgctgtccaa
361 gagaatgtca tgctgggaac gccatcatcg gtggtgttag cttcacatgc ttctgcagct
421 gagcttgcag aatagagaaa atgagctca taatttgctt tgagagctac aggaaatggt
481 tgtttctcct atactttgtc cttaacatct ttcttgatcc taaatatata tctcgtaaca
541 ag
```

SEQ ID NO: 8: ,,Amino Acid sequence of HNP-4"

```
Signal peptide postion 1 to 19
proprotein     postion 20 to 97
mature peptide position 64 to 97

1 mriiallaai llvalqvrag plqargdeap gqeqrgpedq disisfawdk ssalqvsgst
61 rgmvcscrlv fcrrtelrvg ncliggvsft ycctrvd
```

All amino acid sequences above are presented in the one letter code.

The invention is, however, not limited to the precise α-defensins/HNPs described herein above by their concrete sequences but also the use of fragments (functional fragments comprising at least 6 or 8, preferably at least 10, more preferably at least 12, more preferably at least 14 amino acids or coding nucleic acid molecules comprising at least 18 or 24 more preferably at least 30, more preferably at least 36 and more preferably at least 42 coding nucleotides) of the sequences given above and represented in the appended sequence protocol are envisaged. As will be detailed below, also mutated but functional α-defensins/HNPs as well as functional homologues are envisaged in the uses and methods described herein.

α-defensins or HNPs to be employed in context of the present invention are not only naturally occurring and purified α-defensin and HNPs, but may also be produced synthetically, chemically or recombinantly. Preferably said α-defensins and HNPs are purified by standard methods after their chemical or recombinant synthesis or from natural sources, like human blood, in particular from leuckocytes. Corresponding methods are known in the art, e.g. chemical synthesis is described in Raj, Biochem J. 347 (2000), 633, recombinant production, for example in E. coli or in the baculovirus expression system, is known from Piers, Gene 134 (1993), 7-13 and Valore, J. Clin. Invest. 97 (1996), 1624.

It is of note that the present invention provides the use of alpha-defensins and HNPs, whereby also mammalian homologues of the human alpha-defensins as described herein may be employed. The homologues comprise, but are not limited to, the alpha-defensins or HNPs from mouse, guinea pig, rabbit, pig, horse, cow or other primates. Some homologues are depicted in FIG. 4. Also envisaged is the use of synthetic alpha-defensins or HNPs, which comprise, but are not limited to peptides which have the above recited HNP characteristics, namely, a positive charge, beta-sheets, intramolecular disulfide bridges and the anthrax lethal factor recognition motif.

In context of the present invention, the term "identity" or "homology" as used herein relates to a comparison of nucleic acid molecules (nucleotide stretches; DNA, RNA) or amino acid molecules (peptides; proteins; protein-fragments).

The invention also relates to the use of alpha-defensins and HNPs which comprise a mutation in a nucleotide sequence which is complementary to the whole or a part of one of the above-mentioned sequences encoding for the alpha-defensins and HNPs. Said mutant is to be sued in accordance with this invention when it is a "functional mutant". Such a functional mutant, like a functional fragment as defined herein should be capable of binding and/or inhibiting *B. anthracis* toxin. Corresponding examples how the person skilled in the art can test said functionality are given in the experimental part of this invention and herein below.

In order to determine whether a nucleic acid sequence has a certain degree of identity to the nucleic acid sequence encoding an alpha-defensin and HNP the skilled person can use means and methods well-known in the art, e.g., alignments, either manually or by using computer programs such as those mentioned further down below in connection with the definition of the term "hybridization" and degrees of homology.

For example, BLAST2.0, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments. BLAST produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence indentity} \times \% \text{ maximum } BLAST \text{ score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules.

The present invention also relates to alpha-defensin- and HNP-mutants comprising mutations in nucleic acid molecules which hybridize to one of the above described nucleic acid molecules and which encode an alpha-defensin/HNP.

The term "hybridizes" as used in accordance with the present invention may relate to hybridization under stringent or non-stringent conditions. If not further specified, the conditions are preferably non-stringent. Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Such fragments may represent nucleic acid sequences which encode a UpK as defined herein and which have a length of at least 12 nucleotides, preferably at least 15, more preferably at least 18, more preferably of at least 21 nucleotides, more preferably at least 30 nucleotides, even more preferably at least 40 nucleotides and most preferably at least 60 nucleotides. Furthermore, nucleic acid molecules which hybridize with any of the aforementioned nucleic acid molecules also include complementary fragments, derivatives and allelic variants of these molecules.

Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

The term "hybridizing sequences" preferably refers to sequences which display a sequence identity of at least 40%, preferably at least 50%, more preferably at least 60%, even more preferably at least 70%, particularly preferred at least 80%, more particularly preferred at least 90%, even more particularly preferred at least 95%, 97% or 98% and most preferably at least 99% identity with a nucleic acid sequence as described above encoding an alpha-defensin/HNP. Moreover, the term "hybridizing sequences" refers to sequences encoding an alpha-defensin/HNP having a sequence identity of at least 50%, preferably at least 60%, preferably at least 70%, preferably at least 80%, more preferably at least 90%, even more preferably at least 95%, and most preferably at least 99% identity with an amino acid sequence of an alpha-defensin/HNP as disclosed herein. In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., 70-95% identity, more preferably at least 95%, 97%, 98% or 99% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably the described identity exists over a region that is at least about 5 to 30 amino acids or nucleotides in length, more preferably, over a region that is about 5 to 30 amino acids or nucleotides in length. Those having skill in the art will know how to determine percent identity between/among sequences using, for example, algorithms such as those based on CLUSTALW computer program (Thompson, Nucl. Acids Res. 2 (1994), 4673-4680) or FASTDB (Brutlag, Comp. App. Biosci. 6 (1990), 237-245), as known in the art.

Again, functional α-defensins (e.g. HNPs) as well as functional fragments thereof in context of uses and methods described herein may be deduced by methods provided in the appended examples and herein below.

HNPs are multifunctional peptides. Besides their well established capacity to kill a variety of microbial pathogens, immunoenhancing capabilities have been also reported in HNPs. Human neutrophil α-defensins show chemotactic activities for monocytes, T cells and dendritic cells. They enhance the production of antigen specific antibodies and certain cytokines by immune; Yang, (2002) Trends Immunol 23, 291. Yet, the data provided in the experimental part of this invention surprisingly show that alpha-defensin and in particular HNPs are very potent in the neutralization of toxic bacterial enzymes. The structural characteristics of HNPs such as overall dimensions, positive charge, β-sheet, and disulfide bonds are reminiscent of various snake, scorpion, and spider toxins. One intriguing feature of HNPs as LF inhibitors is that HNP-1-3 have the consensus sequence, ++++xhx↓h, which is required for cleavage by LF. Without being bound by theory and based on the data presented herein, it is assumed that the stabilized compact structure of HNPs by disulfide bridges represents the determinant for avoiding cleavage by LF. Yet, HNPs may also bind to regions other than the catalytic center of LF, like uncompetitive and noncompetitive inhibitors.

The experimental data provided in this invention do not only reveal that the human immune system produces potent inhibitors for LF, but also demonstrate the potency of alpha-defensins, preferably of HNPs 1 to 4 and in particular of HNP-1, 2 and 3, for therapy of anthrax (i.e. the medical intervention in an anthrax infection/B. anthracis infection). Although B. anthracis itself can be treated by antibiotics, this frequently fails if not initiated promptly after infection, because even after bacterial eradication, secreted toxins will remain active. The situation is even worse with drug resistant strains, either naturally evolved or manipulated on purpose; Stepanov, (1996). *J Biotechnol* 44, 155. These obstacles underscore the need for novel intervention strategies against anthrax. Indeed, recently, new strategies have been exploited. Treatment with a bacteriophage enzyme, lysin, can circumvent the threat of multi-drug resistant *B. anthracis*, (Schuch, (2002) *Nature* 418, 884) but will not achieve neutralization of anthrax toxin in the circulation. The alpha-defensins and in particular the HNPs described here have therapeutic advantages over other candidates, especially candidates which have been proposed in the medical intervention of anthrax. As documented in the appended examples, the alpha-defensins, in particular the HNPs described herein, can neutralize anthrax LeTx in addition to their function as broad-spectrum antimicrobial peptides and immunoenhancing activities facilitating the initiation of adaptive immune responses. Accordingly, the alpha-defensins/HNPs are particularly useful in the medical intervention of *B. anthracis* infections. Most preferably, they are used in combination with further treatment of the said *B. anthracis* infection, for example in combination with antibiotics. Such a combination therapy may comprise the administration of the alpha-defensin or the HNPs described herein before, during or after the administration of said further medicament.

As pointed out above, it is envisaged that the alpha-defensins/HNPs to be used in accordance with this invention are in form of a peptide or in form of a coding nucleic acid molecule encoding such an alpha-defensins/HNP. Accordingly, the nucleic acid molecule is in particular useful in gene therapy approaches. The term "peptide" in context of this invention does not only comprise peptides as identified herein above in form of SEQ ID Nos. 2, 4, and 6, but also relate to peptides which have a sequence identity of at least 50%, preferably at least 60%, preferably at least 70%, preferably at least 80%, more preferably at least 90%, even more preferably at least 95%, and most preferably at least 99% identity with an amino acid sequence of an alpha-defensin/HNP as disclosed herein, in particular identity to the HNPS as defined in SEQ ID NOs 2, 4, and 6. Also envisaged in context of this invention are alpha-defensins/HNPs which are recombinantly produced (as for example shown in Piers, Gene 134 (1993), 7-13 and Valore, J. Clin. Invest. 97 (1996), 1624) or which are synthetically produced. Methods for the synthetic production of peptides are well known in the art and, inter alia, illustrated in WO 2004/050686. One of these methods comprises for example solid phase synthesis, as e.g. provided by Schnolzer (1992), Int. J. Pept. Protein Res. 40, 180-193. Further methods have been mentioned above, see Raj (2000), loc. cit., Piers (1993) loc. cit. or Valore (1996), loc. cit. The nucleic acid molecules to be used in accordance with this invention may be, e.g., DNA, cDNA, RNA or synthetically produced DNA or RNA or a recombinantly produced chimeric nucleic acid molecule comprising any a polynucleotide encoding an alpha-defensin/HNP as defined herein.

The alpha-defensins/HNPs to be used in accordance with this invention may also be in form of a fusion protein/fusion peptide or a nucleic acid molecule coding for such a fusion protein/fusion peptide. Said fusion protein/peptide may comprise merely a functional fragment of an alpha-defensin/HNP. Said functional fragment/peptide, like mutant versions or homologues versions of said alpha-defensins/HNPs should be capable of binding to/inhibiting *B. anthracis* LeTx ("lethal toxin"). Such an inhibition or binding may be deduced by methods provided in the experimental part of this invention. Accordingly, pharmaceutical composition/medicament to be manufactured comprises the alpha-defensins/HNP(s) or functional parts thereof. Such a functional part is a part which is capable to bind/and or inhibit LeTx, namely the combination of "lethal factor" (LF) and "protective antigen" (PA). Corresponding test for such functionality are provided in the experimental part of this invention.

As documented in the appended examples, the efficacy of a given α-defensin in the uses and methods described herein may be tested and/or verified in vitro and in vivo. For example the potency of a given α-defensin as defined herein in the protection of e.g. macrophages against cytolysis by anthrax LeTx may be measured in vitro. Also the cleavage of MKK by LF in the presence or absence of a given α-defensin is indicative for the usefulness of a given α-defensin in the medical intervention of anthrax. Also in vivo experiments can be carried out. These experiments comprise, but are not limited to, protection assays of non-human test animals, like mice (for example Balb/c mice) from LeTx intoxication. Corresponding examples are given in the experimental part. Further in vivo experiments comprise the infection of test animals like mice, preferably Balb/c mice or C57BL/6J mice with *B. anthracis* spores (via intranasal or intratracheal route), followed by an intravenous injection of α-defensins, like HNP-1, -2, -3, or -4, most preferably HNP-1, -2 or -3.

The pharmaceutical composition/medicament to be manufactured in accordance with the present invention may be used for effective therapy of infected humans and animals and/or for vaccination purposes.

The pharmaceutical composition of the present invention may further comprise a pharmaceutically acceptable carrier, excipient and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg per dose; however, doses below or above this exemplary range are envisioned, especially considering the aforementioned factors. Administration of the suitable compositions may be effected by different ways, e.g., by intravenous, intraperitoneal, subcutaneous, intramuscular, topical or intradermal administration. If the regimen is a continuous infusion, it should also be in the range of 1 μg to 10 mg units per kilogram of body weight per minute, respectively. Progress can be monitored by periodic assessment. The compositions of the invention may be administered locally or systemically. Administration will generally be parenterally, e.g., intravenously. Yet, in a preferred embodiment, the pharmaceutical composition/medicament is also to be administered intrabronchially and/or intra-nasally. Such an administration may comprise the use of sprays comprising alpha-defensins/HNPs (or functional fragments thereof). The alpha-defensins/HNPs may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as antibiotics, protective medicaments or vaccines. Corresponding examples are given herein below.

The alpha-defensins/HNPs (in form of proteins, nucleic acid molecules, fusion proteins or functional fragments of said proteins, nucleic acid molecules or fusion proteins) used in a pharmaceutical composition may be formulated e.g. as neutral or salt forms. Pharmaceutically acceptable salts, such as acid addition salts, and others, are known in the art.

The present invention also provides for a method of treating, preventing or ameliorating a disease caused by *B. anthracis* comprising administering to a subject in need of such a treatment, prevention or amelioration on alpha-defensin or an HNP as defined herein. Preferably, the subject to be treated is a human subject and said *B. anthracis* caused disease is anthrax.

As also discussed for the uses described in this invention, the alpha-defensin or the HNP is most preferably to be administered to a subject or a subject in form of a co-therapy. Said co-therapy, may, inter alia, comprise additional use of antibiotics, the use of protective medicaments or the use of a vaccine.

Antibiotics to be employed are known ion the art and comprise, e.g. fluoroquinolone, macrolides or beta-lactames. In a preferred embodiment of the invention said antibiotic may be selected from the group consisting of ciprofloxacin, ofloxacin, levofloxacin, moxifloxacin, garenoxacin, erythromycin, telithromycin, tetracycline, minocycline, vancomycine, linezolid, doxycycline, penicillin, rifampin, vancomycin, imipenem, chloramphenicol, clindamycin, clarithromycin, quinupristin/dalfopristine and or novel fluoroquinolone antibiotics, as for example, disclosed in GB 239417798.

Further protective medicament to be co-administered to a patient in need of such a treatment or amelioration of a *B. anthracis* caused disease comprises, inter alia, the heptameric anthrax Protective Antigen (PA) as described in Zhang (2004), Biochemistry 43, 6339-6343 or anthrax antitoxins as described in WO 2004/052277, PlyG lysine derived from γ-bacteriophage, PA-specific antibodies, soluble receptor baxed antitoxins, polyvalent inhibitors (PVI), dominant-negative forms of PA (DN-PA), 2,3 alkylcarbonyloxybenzoic acid (as described in WO 2004/032825), peptide LF inhibitors (see Tonello (2002) Nature 418, 286) or chemical LF inhibitors (see Panchal (2004) Nat Struc Mol Bio. 11, 67; Min (2004) Biotechnol. 22, 717).

Based on recent progress in understanding the mechanisms of anthrax toxin, new therapeutic candidates have been designed, such as recombinant antibodies against the toxin (Maynard (2002) *Nat Biotechnol* 20, 597), peptide (Tonello (2002) *Nature* 418, 386; Turk (2004). *Nat Struct Mol Biol* 11, 60) or small chemical inhibitors of LF (Panchal (2004). loc.cit; Min, (2004) loc.cit), polyvalent inhibitors of PA-LF interactions (Mourez (2001) *Nat Biotechnol* 19, 958) and dominant negative mutants of PA (Sellman, (2001), *Science* 292, 695).

The invention also comprises the use or the methods as disclosed herein above, wherein the alpha-defensin/HNPs is to be administered in combination with a vaccine against *B. anthracis*. Accordingly, such a vaccine is an anthrax vaccine, which may inter alia, be selected from the group consisting of a vaccine which is or which is derived from an alternated strain of *B. anthracis* (AVA), *B. anthracis* Protective Antigen (for example rPA describe in WO 2002/100340] or β(1,3) glucans (see for example, US 2004/014715)

The figures show:

FIG. 1A-D. Human α-defensins protect macrophages against cytolysis by anthrax LeTx. A. HNP-1-3 residues are aligned with identified LF substrates: '+' indicates basic residue, 'h' indicates hydrophobic amino acid. B. RAW 264.7 cells were treated with LeTx (400 ng/ml LF and 1600 ng/ml PA) in the presence of indicated amounts of HNP-1,-2 or LL-37. (○). Cell viability was determined by MTT assay: HNP-1 (■), HNP-1 plus LeTx (□); HNP-2 (▲), HNP-2 plus LeTx (Δ); LL-37 (●), LL-37 plus LeTx (○). C. RAW 264.7 cells were treated with LeTx (400 ng of LF and 1600 ng of PA/ml) in the presence of 7 μM HNP-1 or LL-37. Five hours after treatment, cells were stained with trypan blue. D. Viability of RAW 264.7 cells was determined by MTT assay after treatment with LeTx and various concentration of HNP-1. This assay was performed in medium supplemented with 5% FCS: HNP-1 (■), HNP-1 plus LeTx (□).

FIG. 2A-D. HNP-1 inhibits cleavage of a MKK by LF. A. LeTx was treated to RAW 264.7 macrophages with (+) or without (−) HNP-1. At the indicated time points, the cell lysates were prepared and assessed by Western blot with anti-MKK3 antibody. B. In vitro translated MKK3b was incubated for 1 hr with indicated amounts of LF and either HNP-1 or Magainin I. Cleavage of Mkk3b was analyzed by SDS-PAGE and autoradiography C. Raw 264.7 cells were incubated with HNP-1 at 37° C. After 1 hr, the medium was removed and replaced with fresh medium containing LeTx (400 ng/ml LF and 1600 ng/ml PA). Cells were incubated further at 37° C. for 5 hrs. The viability was determined by MTT assay: HNP-1 (■), HNP-1 plus LeTx (□). D. RAW 264.7 cells were treated (+) with LeTx and HNP-1. Two hours after the treatment, cells were stimulated with 10 μg/ml *B. subtilis* LTA for 30 min and the lysates were assessed by immunoblot with antibodies against MAPKs (Total) and their phosphorylated forms (Phospho).

FIG. 3. HNP-1-3 protects Balb/c mice from LeTx intoxication. Three mice per group received LeTx (50 μg of LF plus 50 μg of PA) i.v. before receiving PBS, 500 μg purified HNP-1-3 or 500 μg LL-37 i.v. Animals were monitored for 10 days.

FIG. 4. Mammalian homologues of human α-defensins.

The invention will now be illustrated by but is not limited to the following examples.

EXAMPLE 1

Materials and Methods Used in this Study

Synthetic Peptides and Recombinant Proteins

Synthetic HNP-1 and -2 were obtained from Bachem. For the mouse experiment, HNP-1-3 was purified from human buffy coats. Synthetic LL-37 was generously provided by Dr. Hubert Kalbacher (University of Tübingen). Recombinant LF and PA were purchased from Calbiochem or purified from recombinant *B. anthracis* strains kindly provided by Dr. Stephen H. Leppla (NIH).

Cytotoxicity Assay

One day before the assay, RAW264.7 cells were seeded in a 96 well plate at a density of $3 \times 10^4$ cells per well in RPMI medium containing serum. For the assay, 400 ng/ml LF, 1600 ng/ml PA and described amounts of HNPs were added simultaneously to cells in serum-free RPMI or RPMI supplemented with 5% FCS. Five hours after treatment, cell viability was determined by methyl thiazole tetrazolium (MTT) assay.

In vitro MKK3b Cleavage Assay $S^{35}$ labeled MKK3b was in vitro translated from pcDNA-MKK3b (with kind help of Dr. Jiahuai Han, the Scripps Research Institute) using TNT® quick coupled transcription/translation systems (Promega). In vitro translated MKK3b was incubated at 37° C. for 1 hr in reaction buffer (20 mM Hepes, 1 mM $CaCl_2$, pH 7.2) with indicated amounts of LF and either HNP-1 or Magainin I.

Mouse Protection Experiment

Seven to 9 weeks old female BALB/c mice were treated with LeTx (50 μg of LF and 50 μg of PA in 0.2 ml PBS) i.v. into one tail vein, immediately followed by i.v. injection with the indicated doses of purified HNP-1-3 or synthetic LL-37 diluted in 0.2 ml PBS into the other tail vein. Survival of mice was monitored for 10 days after toxin treatment. Experiments were conducted according to the German animal protection law.

EXAMPLE 2

Cytolysis of RAW 264.7 by LeTx

The murine macrophage cell line, RAW 264.7, is commonly used for LF assay because it is highly sensitive to cytolysis caused by LeTx. When these cells were treated with LeTx, they succumbed to the toxin within a few hours. In marked contrast, the co-treatment with HNP-1 completely abolished cytotoxicity (FIGS. 1B and 1C). This HNP-1 mediated protection was observed even 24 hrs after LeTx treatment (data not shown). HNP-2 (FIG. 1B) and purified HNP-1-3 mixture from human leukocytes (data not shown) showed similar protection whereas LL-37, another neutrophil cationic peptide with a similar size and net charge like HNPs, did not display any significant effect (FIGS. 1B and 1C). To examine whether this phenomenon is physiologically relevant and to assess potential effects of serum components, we performed the same assay under serum-supplemented conditions. In the presence of 5% fetal calf serum (FCS), HNP-1 still protected cells from LeTx induced cytotoxicity, although slightly higher amount of HNP-1 was needed (FIG. 1D).

EXAMPLE 3

Cleavage of MKKS by LeTX and Corresponding Inhibition Experiments

Because LF is a protease, which cleaves the N-terminus of MKKs, it was investigated whether HNP-1 inhibited cleavage of MKK3b in LeTx treated cells. RAW 264.7 macrophages were treated with LeTx (400 ng/ml LF and 1600 ng/ml PA) and HNP-1 (7 μM) for 1 or 2 hrs, and the cell lysates were analyzed using an antibody directed against the C-terminal end of MKK3. Within 2 hrs of LeTx treatment, MKK3b was almost completely converted to its cleaved form but this cleavage was efficiently inhibited by HNP-1 (FIG. 2A).

To verify whether HNP-1 directly inhibits endoprotease activity of LF, an in vitro cleavage assay with $S^{35}$-labeled LF substrate (FIG. 2B) was performed. In vitro translated MKK3b was almost completely cleaved within 1 hr by 500 ng of LF but in the presence of 10 μM HNP-1, proteolysis was efficiently inhibited, suggesting that HNP-1 inactivates the catalytic activity of LF. Other cationic antimicrobial peptides, Magainin I (FIG. 2B) and LL-37 (data not shown) did not prevent cleavage of MKK3b mediated by LF.

EXAMPLE 4

Dose-Dependant Prevention of LeTX Toxicicity

Potential LF inhibitors would be expected to enter cells to exert their activity against LF, and HNPs can, indeed, be internalized into host cells; Nassar et al., *Blood* 100, 4026 (2002). Given the described effects of HNP-1 on LeTx, it was investigated whether HNP-1 can inhibit LF inside cells. Raw 264.7 cells were incubated with HNP-1 at 37° C. for 1 hr, washed extensively to remove free HNP-1 and subsequently treated with LeTx (400 ng/ml LF and 1600 ng/ml PA) at 37° C. for 5 hrs. As shown in FIG. 2C, pre-treatment of macrophages with HNP-1 prevented LeTx toxicity in a HNP-1 dose dependent manner, indicating that HNP-1 acts on LeTx inside cells.

LeTx inhibits extracellular signal-regulated kinase (ERK) and p38 MAPK signaling through cleavage of members of MKK family in activated macrophages; Park (2002), *Science* 297, 2048. To characterize the effects of HNP-1 on LeTx mediated impairment of MAPK signaling, macrophages were incubated with LeTx (200 ng/ml LF and 1600 ng/ml PA) and HNP-1 (30 μM) for 2 hrs, followed by stimulation with *B. subtilis* lipoteichoic acid (LTA). This experiment was performed in 5% FCS supplemented conditions to achieve efficient stimulation of toll-like receptors (TLR) by LTA. LeTx strongly inhibited ERK and p38 activation in macrophages and phosphorylation of these two MAPKs was restored by HNP-1 (FIG. 2D).

EXAMPLE 5

Therapeutic Intervention against an Anthrax Attack

Having identified LeTx neutralization as a novel function of HNPs, we decided to evaluate this activity for therapeutic intervention against anthrax attack. To this end, LeTx sensitive Balb/c mice received LeTx (50 μg LF and 50 μg PA) intravenously (i.v.), immediately followed by the indicated amounts of purified HNP-1-3 i.v. (FIG. 3). Within 2 days, the mice succumbed to the toxin. In contrast, 500 μg of HNP-1-3 protected mice from intoxication up to 10 days after LeTx treatment. LL-37, a control antimicrobial peptide, had no effect on LeTx toxicity (FIG. 3).

The invention claimed is:

1. A method of treating a disease caused by *Bacillus anthracis* (*B. anthracis*) comprising administering to a subject in need of such a treatment an effective amount of a human neutrophil protein (HNP) selected from the group consisting of human neutrophil protein 1 (HNP-1), human neutrophil protein 2 (HNP-2), human neutrophil protein 3 (HNP-3) and human neutrophil protein 4 (HNP-4).

2. The method of claim 1, wherein said subject is a human subject.

3. The method of claim 1, wherein said disease caused by *B. anthracis* is anthrax.

4. The method of claim 1, wherein said human neutrophil protein 1 (HNP-1), human neutrophil protein 2 (HNP-2), human neutrophil protein 3 (HNP-3) or human neutrophil protein 4 (HNP-4) is selected from the group consisting of (a) a polypeptide or peptide having the amino acid sequence as shown in SEQ ID NO: 2, SEQ ID NO: 4, SEQ ID NO: 6 or SEQ ID NO: 8;

(b) a polypeptide or peptide encoded by a nucleic acid molecule having the DNA sequence as shown in SEQ ID NOS: 1, 3, 5 or 7; and (c) a polypeptide or peptide encoded by a nucleic acid molecule hybridizing under high stringency conditions of 0.1×SSC (saline sodium citrate buffer), 0.1% SDS (sodium dodecyl sulfate) at 65° C. to the complementary strand of nucleic acid molecules having the DNA sequence as shown in SEQ ID NOS: 1, 3, 5 or 7.

5. The method of claim 1, wherein said HNP is administered to a subject with a co-therapy.

6. The method of claim 5, wherein said co-therapy is administration of an antibiotic selected from the group consisting of fluoroquinolones, macrolides and beta-lactames.

7. The method of claim 6, wherein said antibiotic is selected from the group consisting of ciprofloxacin, ofloxacin, levofloxacin, moxifloxacin, garenoxacin, erythromycin, telithromycin, tetracycline, minocycline.vancomycine, linezolid, doxycycline, penicillin, rifampin, vancomycin, imipenem, chloramphenicol, clindamycin, clarithromycin and quinupristin/dalfopristine.

8. The method of claim 5, wherein said co-therapy is administration of a protective medicament selected from the group consisting of the heptameric anthrax Protective Antigen (PA), anthrax antitoxins, PlyG lysine, PA-specific antibodies, soluble receptor based antitoxins, polyvalent inhibitors (PVI), dominant-negative forms of PA (DN-PA), 2,3 alkylcarbonyloxybenzoic acid, Peptide lethal factor (LF) inhibitors and chemical lethal factor (LF) inhibitors.

9. The method of claim 5, wherein said co-therapy is administration of a vaccine which is selected from (i) an altered strain of *B. anthracis* (AVA), (ii) *B. anthracis*, (iii) Protective Antigen or (iv) β(1,3)glucans.

* * * * *

SEQUENCE LISTING

```
<160> NUMBER OF SEQ ID NOS: 24

<210> SEQ ID NO 1
<211> LENGTH: 490
<212> TYPE: DNA
<213> ORGANISM: homo sapiens
<220> FEATURE:
<221> NAME/KEY: CDS
<222> LOCATION: (81)..(365)

<400> SEQUENCE: 1
ctatagaaga cctgggacag aggactgctg tctgccctct ctggtcaccc tgcctagcta       60
gaggatctgt gacccccagcc atg agg acc ctc gcc atc ctt gct gcc att ctc      113
                       Met Arg Thr Leu Ala Ile Leu Ala Ala Ile Leu
                        1               5                      10 ctg gtg gcc ctg cag gcc cag gct gag cca ctc cag gca aga gct gat         161
Leu Val Ala Leu Gln Ala Gln Ala Glu Pro Leu Gln Ala Arg Ala Asp
            15                  20                  25 gag gtt gct gca gcc ccg gag cag att gca gcg gac atc cca gaa gtg         209
Glu Val Ala Ala Ala Pro Glu Gln Ile Ala Ala Asp Ile Pro Glu Val
        30                  35                  40 gtt gtt tcc ctt gca tgg gac gaa agc ttg gct cca aag cat cca ggc         257
Val Val Ser Leu Ala Trp Asp Glu Ser Leu Ala Pro Lys His Pro Gly
    45                  50                  55
```

| | | | | | | | | | | | | | | | |
|---|---|---|---|---|---|---|---|---|---|---|---|---|---|---|---|
| tca | agg | aaa | aac | atg | gcc | tgc | tat | tgc | aga | ata | cca | gcg | tgc | att | gca | 305 |
| Ser | Arg | Lys | Asn | Met | Ala | Cys | Tyr | Cys | Arg | Ile | Pro | Ala | Cys | Ile | Ala |
| 60 | | | | 65 | | | | 70 | | | | 75 | | | |

| | | | | | | | | | | | | | | |
|---|---|---|---|---|---|---|---|---|---|---|---|---|---|---|
| gga | gaa | cgt | cgc | tat | gga | acc | tgc | atc | tac | cag | gga | aga | ctc | tgg | gca | 353 |
| Gly | Glu | Arg | Arg | Tyr | Gly | Thr | Cys | Ile | Tyr | Gln | Gly | Arg | Leu | Trp | Ala |
| | | | | 80 | | | | 85 | | | | 90 | | | | ttc tgc tgc tga gcttgcagaa aagaaaaat gagctcaaaa tttgctttga     405
Phe Cys Cys gagctacagg gaattgctat tactcctgta ccttctgctc aatttccttt cctcatccca   465
aataaatgcc ttggtacaag aaaag     490

<210> SEQ ID NO 2
<211> LENGTH: 94
<212> TYPE: PRT
<213> ORGANISM: homo sapiens

<400> SEQUENCE: 2

Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Ser Leu Ala
        35                  40                  45

Trp Asp Glu Ser Leu Ala Pro Lys His Pro Gly Ser Arg Lys Asn Met
50                  55                  60

Ala Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90

<210> SEQ ID NO 3
<211> LENGTH: 87
<212> TYPE: DNA
<213> ORGANISM: homo sapiens

<400> SEQUENCE: 3
tgctattgca gaataccagc gtgcattgca ggagaacgtc gctatggaac ctgcatctac   60
cagggaagac tctgggcatt ctgctgc     87

<210> SEQ ID NO 4
<211> LENGTH: 29
<212> TYPE: PRT
<213> ORGANISM: homo sapiens

<400> SEQUENCE: 4

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 5
<211> LENGTH: 487
<212> TYPE: DNA
<213> ORGANISM: homo sapiens
<220> FEATURE:
<221> NAME/KEY: CDS
<222> LOCATION: (86)..(370)

<400> SEQUENCE: 5
ccttgctata gaagacctgg gacagaggac tgctgtctgc cctctctggt caccctgcct   60

```
agctagagga tctgtgaccc cagcc atg agg acc ctc gcc atc ctt gct gcc      112
                               Met Arg Thr Leu Ala Ile Leu Ala Ala
                                 1               5 att ctc ctg gtg gcc ctg cag gcc cag gct gag cca ctc cag gca aga     160
Ile Leu Leu Val Ala Leu Gln Ala Gln Ala Glu Pro Leu Gln Ala Arg
 10              15                  20                  25 gct gat gag gtt gct gca gcc ccg gag cag att gca gcg gac atc cca     208
Ala Asp Glu Val Ala Ala Ala Pro Glu Gln Ile Ala Ala Asp Ile Pro
             30                  35                  40 gaa gtg gtt gtt tcc ctt gca tgg gac gaa agc ttg gct cca aag cat     256
Glu Val Val Val Ser Leu Ala Trp Asp Glu Ser Leu Ala Pro Lys His
         45                  50                  55 cca ggc tca agg aaa aac atg gac tgc tat tgc aga ata cca gcg tgc     304
Pro Gly Ser Arg Lys Asn Met Asp Cys Tyr Cys Arg Ile Pro Ala Cys
     60                  65                  70 att gca gga gaa cgt cgc tat gga acc tgc atc tac cag gga aga ctc     352
Ile Ala Gly Glu Arg Arg Tyr Gly Thr Cys Ile Tyr Gln Gly Arg Leu
 75                  80                  85 tgg gca ttc tgc tgc tga gcttgcagaa aagaaaaat gagctcaaaa             400
Trp Ala Phe Cys Cys
 90 tttgctttga gagctacagg gaattgctat tactcctgta ccttctgctc aatttccttt   460 cctcatctca aataaatgcc ttgttac                                       487

<210> SEQ ID NO 6
<211> LENGTH: 94
<212> TYPE: PRT
<213> ORGANISM: homo sapiens

<400> SEQUENCE: 6

Met Arg Thr Leu Ala Ile Leu Ala Ala Ile Leu Leu Val Ala Leu Gln
 1               5                  10                  15

Ala Gln Ala Glu Pro Leu Gln Ala Arg Ala Asp Glu Val Ala Ala Ala
             20                  25                  30

Pro Glu Gln Ile Ala Ala Asp Ile Pro Glu Val Val Val Ser Leu Ala
         35                  40                  45

Trp Asp Glu Ser Leu Ala Pro Lys His Pro Gly Ser Arg Lys Asn Met
     50                  55                  60

Asp Cys Tyr Cys Arg Ile Pro Ala Cys Ile Ala Gly Glu Arg Arg Tyr
 65                  70                  75                  80

Gly Thr Cys Ile Tyr Gln Gly Arg Leu Trp Ala Phe Cys Cys
             85                  90

<210> SEQ ID NO 7
<211> LENGTH: 542
<212> TYPE: DNA
<213> ORGANISM: homo sapiens
<220> FEATURE:
<221> NAME/KEY: CDS
<222> LOCATION: (52)..(345)

<400> SEQUENCE: 7
gtctgccctc tctgctcgcc ctgcctagct tgaggatctg tcaccccagc c atg agg   57
                                                         Met Arg
                                                           1 att atc gcc ctc ctc gct gct att ctc ttg gta gcc ctc cag gtc cgg   105
Ile Ile Ala Leu Leu Ala Ala Ile Leu Leu Val Ala Leu Gln Val Arg
         5                  10                  15 gca ggc cca ctc cag gca aga ggt gat gag gct cca ggc cag gag cag   153
Ala Gly Pro Leu Gln Ala Arg Gly Asp Glu Ala Pro Gly Gln Glu Gln
     20                  25                  30
```

```
cgt ggg cca gaa gac cag gac ata tct att tcc ttt gca tgg gat aaa        201
Arg Gly Pro Glu Asp Gln Asp Ile Ser Ile Ser Phe Ala Trp Asp Lys
 35              40                  45                  50 agc tct gct ctt cag gtt tca ggc tca aca agg ggc atg gtc tgc tct        249
Ser Ser Ala Leu Gln Val Ser Gly Ser Thr Arg Gly Met Val Cys Ser
                 55                  60                  65 tgc aga tta gta ttc tgc cgg cga aca gaa ctt cgt gtt ggg aac tgc        297
Cys Arg Leu Val Phe Cys Arg Arg Thr Glu Leu Arg Val Gly Asn Cys
             70                  75                  80 ctc att ggt ggt gtg agt ttc aca tac tgc tgc acg cgt gtc gat taa        345
Leu Ile Gly Gly Val Ser Phe Thr Tyr Cys Cys Thr Arg Val Asp
         85                  90                  95 cgttctgctg tccaagagaa tgtcatgctg ggaacgccat catcggtggt gttagcttca      405
catgcttctg cagctgagct tgcagaatag agaaaaatga gctcataatt tgctttgaga      465
gctacaggaa atggttgttt ctcctatact ttgtccttaa catctttctt gatcctaaat      525
atatatctcg taacaag                                                     542

<210> SEQ ID NO 8
<211> LENGTH: 97
<212> TYPE: PRT
<213> ORGANISM: homo sapiens

<400> SEQUENCE: 8

Met Arg Ile Ile Ala Leu Leu Ala Ala Ile Leu Leu Val Ala Leu Gln
 1               5                   10                  15

Val Arg Ala Gly Pro Leu Gln Ala Arg Gly Asp Glu Ala Pro Gly Gln
                20                  25                  30

Glu Gln Arg Gly Pro Glu Asp Gln Asp Ile Ser Ile Ser Phe Ala Trp
             35                  40                  45

Asp Lys Ser Ser Ala Leu Gln Val Ser Gly Ser Thr Arg Gly Met Val
 50                  55                  60

Cys Ser Cys Arg Leu Val Phe Cys Arg Arg Thr Glu Leu Arg Val Gly
 65                  70                  75                  80

Asn Cys Leu Ile Gly Gly Val Ser Phe Thr Tyr Cys Cys Thr Arg Val
                 85                  90                  95

Asp

<210> SEQ ID NO 9
<211> LENGTH: 30
<212> TYPE: PRT
<213> ORGANISM: HOMO SAPIENS

<400> SEQUENCE: 9

Ala Cys Tyr Cys Arg Ile Pro Ala Cys Ile Ala Gly Glu Arg Arg Tyr
 1               5                   10                  15

Gly Thr Cys Ile Tyr Gln Gly Arg Leu Trp Ala Phe Cys Cys
                20                  25                  30

<210> SEQ ID NO 10
<211> LENGTH: 29
<212> TYPE: PRT
<213> ORGANISM: homo sapiens

<400> SEQUENCE: 10

Cys Tyr Cys Arg Ile Pro Ala Cys Ile Ala Gly Glu Arg Arg Tyr Gly
 1               5                   10                  15

Thr Cys Ile Tyr Gln Gly Arg Leu Trp Ala Phe Cys Cys
                20                  25
```

```
<210> SEQ ID NO 11
<211> LENGTH: 30
<212> TYPE: PRT
<213> ORGANISM: homo sapiens

<400> SEQUENCE: 11

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 12
<211> LENGTH: 33
<212> TYPE: PRT
<213> ORGANISM: homo sapiens

<400> SEQUENCE: 12

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val

<210> SEQ ID NO 13
<211> LENGTH: 33
<212> TYPE: PRT
<213> ORGANISM: Oryctolagus cuniculus

<400> SEQUENCE: 13

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 14
<211> LENGTH: 33
<212> TYPE: PRT
<213> ORGANISM: Oryctolagus cuniculus

<400> SEQUENCE: 14

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 15
<211> LENGTH: 34
<212> TYPE: PRT
<213> ORGANISM: Oryctolagus cuniculus

<400> SEQUENCE: 15

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg
```

<210> SEQ ID NO 16
<211> LENGTH: 34
<212> TYPE: PRT
<213> ORGANISM: Oryctolagus cuniculus

<400> SEQUENCE: 16

Gly Arg Cys Val Cys Arg Lys Gln Leu Leu Cys Ser Tyr Arg Glu Arg
1               5                   10                  15

Arg Ile Gly Asp Cys Lys Ile Arg Gly Val Arg Phe Pro Phe Cys Cys
            20                  25                  30

Pro Arg

<210> SEQ ID NO 17
<211> LENGTH: 33
<212> TYPE: PRT
<213> ORGANISM: Oryctolagus cuniculus

<400> SEQUENCE: 17

Val Ser Cys Thr Cys Arg Arg Phe Ser Cys Gly Phe Gly Glu Arg Ala
1               5                   10                  15

Ser Gly Ser Cys Thr Val Asn Gly Val Arg His Thr Leu Cys Cys Arg
            20                  25                  30

Arg

<210> SEQ ID NO 18
<211> LENGTH: 33
<212> TYPE: PRT
<213> ORGANISM: Oryctolagus cuniculus

<400> SEQUENCE: 18

Val Phe Cys Thr Cys Arg Gly Phe Leu Cys Gly Ser Gly Glu Arg Ala
1               5                   10                  15

Ser Gly Ser Cys Thr Ile Asn Gly Val Arg His Thr Leu Cys Cys Arg
            20                  25                  30

Arg

<210> SEQ ID NO 19
<211> LENGTH: 31
<212> TYPE: PRT
<213> ORGANISM: RATTUS NORVEGICUS

<400> SEQUENCE: 19

Thr Cys Tyr Cys Arg Arg Thr Arg Cys Gly Phe Arg Glu Arg Leu Ser
1               5                   10                  15

Gly Ala Cys Gly Tyr Arg Gly Arg Ile Tyr Arg Leu Cys Cys Arg
            20                  25                  30

<210> SEQ ID NO 20
<211> LENGTH: 32
<212> TYPE: PRT
<213> ORGANISM: RATTUS NORVEGICUS

<400> SEQUENCE: 20

Val Thr Cys Tyr Cys Arg Ser Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 21
<211> LENGTH: 29
<212> TYPE: PRT
<213> ORGANISM: RATTUS NORVEGICUS

```
<400> SEQUENCE: 21

Cys Ser Cys Arg Thr Ser Ser Cys Arg Phe Gly Glu Arg Leu Ser Gly
1               5                   10                  15

Ala Cys Arg Leu Asn Gly Arg Ile Tyr Arg Leu Cys Cys
            20                  25

<210> SEQ ID NO 22
<211> LENGTH: 31
<212> TYPE: PRT
<213> ORGANISM: RATTUS NORVEGICUS

<400> SEQUENCE: 22

Ala Cys Tyr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30

<210> SEQ ID NO 23
<211> LENGTH: 35
<212> TYPE: PRT
<213> ORGANISM: mus musculus

<400> SEQUENCE: 23

Leu Arg Asp Leu Val Cys Tyr Cys Arg Ser Arg Gly Cys Lys Gly Arg
1               5                   10                  15

Glu Arg Met Asn Gly Thr Cys Arg Lys Gly His Leu Leu Tyr Thr Leu
            20                  25                  30

Cys Cys Arg
        35

<210> SEQ ID NO 24
<211> LENGTH: 31
<212> TYPE: PRT
<213> ORGANISM: Cavia guianae

<400> SEQUENCE: 24

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30
```